(12) United States Patent
Ishizawa et al.

(10) Patent No.: US 7,262,231 B2
(45) Date of Patent: Aug. 28, 2007

(54) PHOTOSENSITIVE AMINE GENERATOR, PHOTOCURABLE COMPOSITION AND PHOTOREACTIVE ADHESIVE COMPOSITION

(75) Inventors: Hideaki Ishizawa, Hirakata (JP); Hiroji Fukui, Kyoto (JP); Takeo Kuroda, Mukoh (JP)

(73) Assignee: Sekisui Chemical Co., Ltd., Osaka (JP)

( * ) Notice: Subject to any disclaimer, the term of this patent is extended or adjusted under 35 U.S.C. 154(b) by 0 days.

(21) Appl. No.: 11/204,635

(22) Filed: Aug. 16, 2005

(65) Prior Publication Data
US 2006/0035995 A1 Feb. 16, 2006

Related U.S. Application Data

(63) Continuation of application No. 10/276,916, filed as application No. PCT/JP01/04370 on May 24, 2001, now abandoned.

(30) Foreign Application Priority Data

| May 25, 2000 | (JP) | 2000-155087 |
| Aug. 21, 2000 | (JP) | 2000-249958 |
| Sep. 4, 2000 | (JP) | 2000-267379 |

(51) Int. Cl.
*C08F 2/50* (2006.01)
*C08K 3/00* (2006.01)

(52) U.S. Cl. ......... 522/182.21; 522/151; 522/153; 522/154; 522/173; 522/174; 522/178; 522/182; 522/183; 522/7; 522/16; 522/28; 522/30; 522/39; 522/53; 522/65; 522/113; 522/114; 522/120; 522/121; 522/152; 522/904; 252/182.11; 252/182.12; 252/182.2; 252/182.22; 252/182.23; 252/182.28

(58) Field of Classification Search .......... 522/7, 522/16, 28, 30, 35, 39, 53, 65, 113, 114, 116, 522/126, 134, 135, 136, 139, 140, 151, 153, 522/154, 173, 174, 178, 182, 183, 120, 121, 522/152, 904; 252/182.11, 182.12, 182.2, 252/182.21, 182.22, 182.23, 182.28
See application file for complete search history.

(56) References Cited

U.S. PATENT DOCUMENTS 3,824,217 A 7/1974 Barker
5,233,003 A 8/1993 Lucas et al.

FOREIGN PATENT DOCUMENTS

| JP | 56-139564 | * 10/1981 |
| JP | 61-258876 | 11/1986 |
| JP | 63-186722 | 8/1988 |
| JP | 07-118547 | 5/1995 |
| JP | 07-173403 | 7/1995 |
| JP | 2000-275834 | 10/2000 |
| WO | WO98/51496 | 11/1998 |
| WO | WO 01/49767 A1 | 7/2001 |

* cited by examiner

*Primary Examiner*—Sanze L. McClendon
(74) *Attorney, Agent, or Firm*—Townsend & Banta

(57) ABSTRACT

The invention provides compounds which can generate amine by irradiation with light and are excellent both in photodecomposability and in reactivity and compatibility with amine-curable compounds, and photo-setting compositions containing the compounds. The compounds are carbamoyloxyimino compounds represented by the structural formula (I); and the compositions each comprise one or more of the carbamoyloxyimino compounds and an amine-curable compound. In the formula (I), R1 is an n-valent organic group; R2 and R3 are each hydrogen or an aromatic or aliphatic group; and n is an integer of 1 or above.

2 Claims, 4 Drawing Sheets
PHOTOSENSITIVE AMINE GENERATOR, PHOTOCURABLE COMPOSITION AND PHOTOREACTIVE ADHESIVE COMPOSITION This is a continuation application of U.S. application Ser. No. 10/276,916, filed Feb. 21, 2003 now abandoned which is based on an international application No. PCT/JP01/04370 with an international filing date of 24 May 2001.

TECHNICAL FIELD

The present invention relates to a photosensitive amine generator, a photocurable composition and a photoreactive adhesive composition.

Known as photosensitive amine generators are a cobalt amine complex, o-nitrobenzyl carbamate, an oxime ester and the like.

However, these photosensitive amine generators are low in quantum yield. For example, a quantum yield of the cobalt amine complex is about 0.01 for a radiation at 254 nm, that of the o-nitrobenzyl carbamate is about 0.13 for a radiation at 254 nm and that of the oxime ester is about 0.3 for a radiation at 366 nm, as described in Bull. Chem. Soc. Jpn., (No. 11), 2495, (1988).

A photocurable resin composition which undergoes curing by a reaction of such a photosensitive amine generator with an amine-curable compound is exemplified by an epoxy resin composition containing an epoxy resin and o-nitrobenzyl carbamate compound as an anionic photoinitiator (Japanese Patent Laying-Open No. Hei 7-70292).

However, the efficiency with which the o-nitrobenzyl carbamate compound is photodecomposed to an amine compound is low. This creates the following problems; the epoxy resin composition must be exposed to a radiation for a prolonged period of time; and a large amount of the o-nitrobenzyl carbamate compound must be added to the epoxy resin to provide a sufficient cure rate.

Meanwhile, adhesives are generally supplied in the liquid form and coated onto an adherend, as by a brush or roller, which is subsequently joined to another adherend. After the joining, the adhesives solidify as a result of solvent evaporation or molecular weight growth, so that the adherends are firmly bonded to each other.

Adhesives exhibit high bond strength. However, they require a troublesome operation by which they are coated onto adherends and need a relatively long time to complete curing. Accordingly, adherends must be provisionally held in contact with each other by some means until the liquid adhesives solidify and exhibit required bond strength. This results in the insufficient workability.

Also, a drying or heating means must be provided to vaporize a solvent. In addition, the solvent once vaporized adversely affects working environments. These have been problems.

A variety of one-part urethane adhesives have been conventionally proposed (for example, in Japanese Patent Laying-Open No. Sho 61-31418). However, a moisture-curing reaction of a urethane prepolymer proceeds insufficiently immediately after such adhesives have combined adherends together. This results in the failure of the one-part urethane adhesives to provide sufficient initial bond strength and heat resistance immediately after combination of adherends.

Japanese Patent Laying-Open No. Sho 64-24821 discloses a photocurable polyurethane composition which contains a polyurethane oligomer having an active isocyanate group, a UV-curable organic compound having a hydroxyl group, and a photoinitiator. This reference describes that a one-part, low-viscosity photocurable polyurethane composition is obtained with the increased workability, which exhibits the increased initial bond strength as a result of a UV-induced curing reaction.

Japanese Patent Publication No. Hei 7-103356 discloses a photocurable polyurethane adhesive comprising (a) a compound having a number average molecular weight of 3,000 or above and containing at least one photopolymerizable double bond in a molecule, (b) a photopolymerizable monomer having a molecular weight of 200-800 and (c) an isocyanate compound, as well as disclosing a bonding method utilizing this adhesive.

However, in the case where a photocurable polyurethane composition utilizing free-radical photopolymerization, such as those disclosed in Japanese Patent Laying-Open No. Sho 64-24821 and Japanese Patent Publication No. Hei 7-103356, is used as an adhesive, the attempt to improve heat resistance of the adhesive immediately after combination of adherends by increasing a photocurable component content thereof or by achieving crosslinking by irradiation has resulted in the problematic reduction of initial bond strength after combination and bond strength after cure.

SUMMARY OF THE INVENTION

It is an object of the present invention to provide a photosensitive amine generator which shows superior photo-decomposability and improved reactivity and compatibility with an amine-curable compound, a photocurable composition containing the amine generator and a photoreactive adhesive composition.

It is other object of the present invention to provide a photoreactive adhesive composition which can solve the problems encountered in the above-described conventional photocurable urethane adhesives, provides high workability for its one-part formulation, cures upon exposure to a radiation and exhibits initial bond strength and heat resistance in a speedy fashion.

In accordance with a broad aspect of a first invention of this application, a photosensitive amine generator is provided which contains a carbamoyloxyimino group and is represented by the following structural formula 1.

In the structural formula 1, R1 is an n-valent organic group, R2 and R3 are independently hydrogen, an aromatic group or an aliphatic group, and n is an integer of 1 or larger.

[Structural Formula 1]

$$R1\left[\begin{array}{c}H\;\;\;O\\|\;\;\;\|\\N-C-O-N=C\end{array}\begin{array}{c}R2\\ \diagup\\ \diagdown\\R3\end{array}\right]_n$$

In a particular aspect of the first invention, R1 in the structural formula 1 is an organic group represented by the following structural formula 2. In the structural formula 2, R4 is an (m+n)-valent organic group, R5 is at

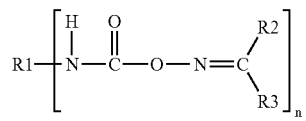

least one selected from the group consisting of isocyanate, (meth)acryloyl and vinyl groups, and m is an integer of 1 or larger. If R5 exists in plurality, R5's may be identical to or different from each other.

[Structural Formula 2]

In the preceding structural formula 1, it is preferred that one of R2 and R3 is hydrogen or an aliphatic group and the other is an aromatic group.

Also in the structural formula 1, R1 is preferably an aromatic group.

In the structural formula 2, R4 is preferably an aromatic group.

Also in the particular aspect of the first invention, R2 and R3 are independently a grouping selected from the group consisting of hydrogen, methyl, phenyl and naphthyl.

A second invention of this application is a photo-sensitive amine generator characterized as comprising a homopolymer of a monomer having a (meth)acryloyl group and a carbamoyloxyimino group, or a polymer or oligomer made by copolymerization of a compound having a free-radically polymerizable group with a monomer having a (meth) acryloyl group and a carbamoyloxyimino group.

A third invention of this application is a photocurable composition characterized as containing the photosensitive amine generator in accordance with the first or second invention and an amine-curable compound. Preferably, the photocurable composition further contains a thioxanthone sensitizer.

The photocurable composition in accordance with the third invention, when exposed to a radiation, generates amine very efficiently. The subsequent reaction between the generated amine and an isocyanate, epoxy, (meth)acryloyl or vinyl group causes the composition to exhibit sufficient initial bond strength, holding power and heat resistance immediately after it has combined adherends. If the isocyanate group remains, the amine-curable compound is then caused to undergo moisture-curing, so that the composition finally exhibits high bond strength.

Further, in the case where the photocurable adhesive composition further contains thioxanthone or its derivative, a photosensitizing effect thereof increases a rate of amine generation when the composition is exposed to a radiation.

According to a fourth invention of this application, a photocurable composition is provided which is characterized as containing:

A: an amine-curable compound, and

B: a photosensitive amine generator having a carbamoyloxyimino group.

The photosensitive amine generator in accordance with the first or second invention can be used as the above-specified compound B in accordance with the fourth invention.

In another particular aspect of the fourth invention, the compound B having a carbamoyloxyimino group is a compound obtained by reacting an isocyanate group of an urethane prepolymer with an oxime compound.

In a further particular aspect of the fourth invention, the compound B having a carbamoyloxyimino group is a compound having a carbamoyloxyimino group and a functional group selected from isocyanate, epoxy and free-radically polymerizable groups.

Preferably, the photocurable composition in accordance with the fourth invention further contains a thioxanthone sensitizer.

The photocurable composition in accordance with the fourth invention, even if exposed to a radiation before it combines adherends together, exhibits high initial bond strength and heat resistance within a short period of time after the combination. Also, it finally exhibits high bond strength.

In accordance with a broad aspect of a fifth invention of this application, a photocurable composition is provided which is characterized as containing:

A: an amine-curable compound,

B': a photosensitive amine generator having a free-radially polymerizable group and a carbamoyloxyimino group, and C: a free-radical photoinitiator.

When the photocurable composition in accordance with the fifth invention is irradiated, the free-radical photoinitiator is activated and the photosensitive amine generator is made into a polymer. Before the irradiation, the photosensitive amine generator assumes a monomeric form. Hence, the photocurable composition before the irradiation has a relatively lower viscosity and is more spreadable. By irradiation, the free-radical photoinitiator is activated and the photosensitive amine generator is made into a polymer and caused to generate amine, so that a reaction between the generated amine and an amine-reactive functional group in the amine-curable compound is initiated. As a result, the composition exhibits excellent initial bond strength and heat resistance within a short time after the irradiation.

In accordance with a broad aspect of a sixth invention of this application, a photocurable composition is provided which is characterized as containing:

A': a urethane prepolymer, and

B: a photosensitive amine generator having a carbamoyloxyimino group.

In a particular aspect of the sixth invention, the compound B having a carbamoyloxyimino group is a polymer or oligomer made via copolymerization of a compound having a free-radically polymerizable group with a monomer having a (meth)acryloyl group and a carbamoyloxyimino group.

In the case where the photosensitive amine generator is a polymer or an oligomer made via copolymerization of a compound having a free-radically polymerizable group with a monomer having a (meth)acryloyl group and a carbamoyloxy-imino group, the suitable choice of the compound having a free-radically polymerizable group results in the increased compatibility thereof with the urethane prepolymer. Also, the introduction of plural carbamoyloxyimino groups into a molecule of the polymer or oligomer increases a cure rate of the photocurable composition.

Also, thioxanthone or its derivative, if present as a free-radical photoinitiator, serves to polymerize the photosensitive amine generator and increase the response thereof to irradiation so that amine is generated with the higher efficiency.

A seventh invention of this application is a photocurable composition characterized as containing:

A': a urethane prepolymer,

B': a photosensitive amine generator having a (meth) acryloyl group and a carbamoyloxyimino group, and C': a free-radical photoinitiator.

Preferably, thioxanthone or its derivative is further contained in the fourth through seventh inventions.

A photoreactive adhesive composition in accordance with the present invention is characterized as comprising the photocurable composition in accordance with any one of the third through seventh inventions.

DETAILED DESCRIPTION OF THE INVENTION

Figure 1:
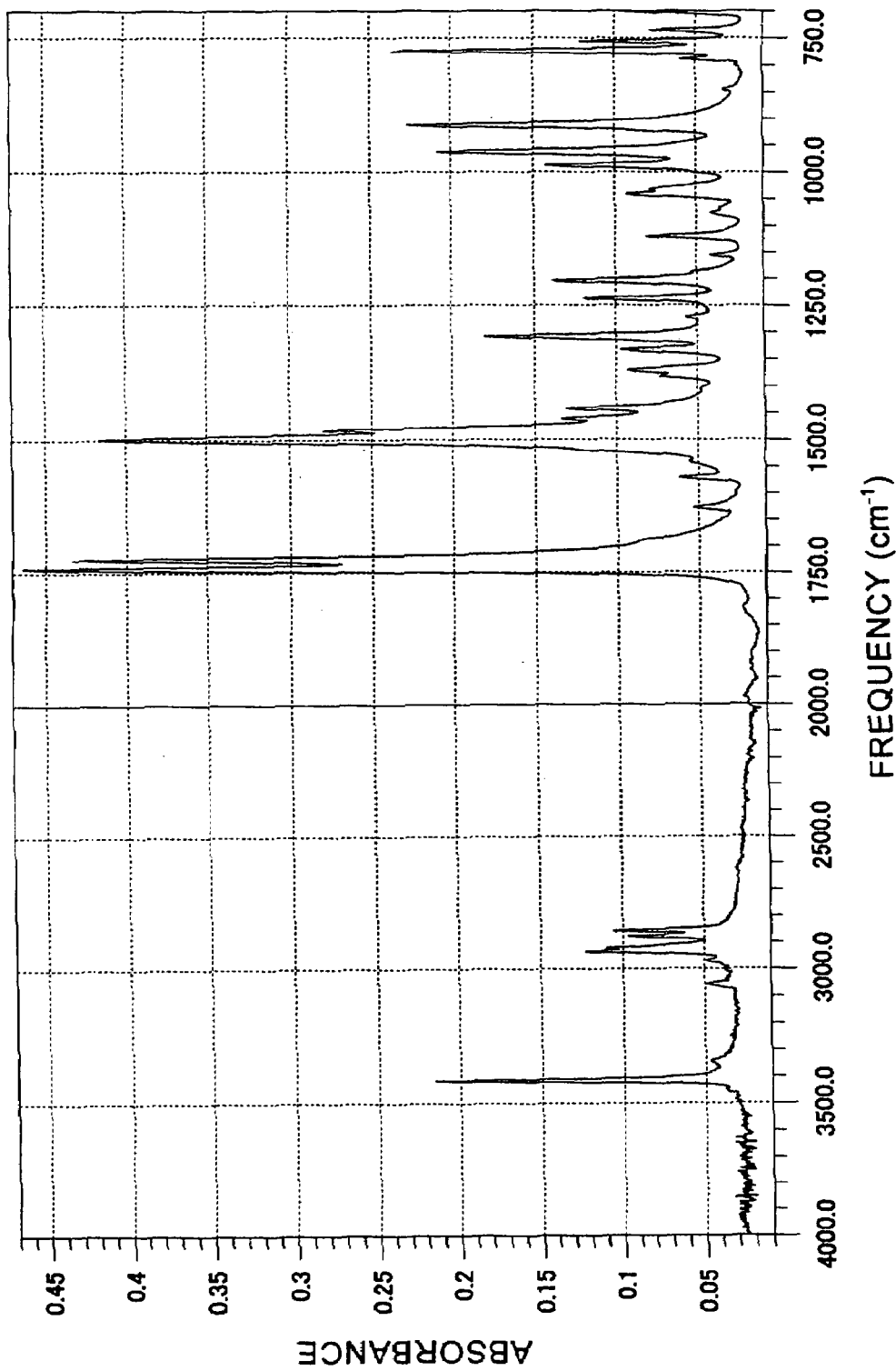
FIG. 1 shows an infrared absorption spectrum of the compound 1 as synthesized in Example 1.

In the structural formula 1 which represents the photosensitive amine generator of the present invention, R1 is an n-valent organic group, preferably an aliphatic group; an aromatic group; or a polymeric backbone such as comprised of polyurethane, polyether or polyester having a bonding valence at its terminal or in its side chain. R2 and R3 are independently hydrogen or an organic group such as an aromatic or aliphatic group, and preferably selected from the group consisting of hydrogen, an alkyl group having 1-10 carbon atoms, a phenyl group, a naphthyl group and substituted phenyl and naphthyl groups.

In the structural formula 1, n is an integer of 1 or larger, preferably 2 or larger. If n is 2 or larger, the photosensitive amine generator is photodecomposed into amine in a more satisfactory manner, and the generated shows the increased reactivity.

If a molecular weight of R1 in the structural formula 1 is excessively low, the compatibility of the photosensitive amine generator with the amine-curable compound decreases. On the other hand, if it is excessively high, the reactivity of the generated amine compound decreases. Accordingly, R1 preferably has a molecular weight of 200-20,000, more preferably 400-10,000, further preferably 400-5,000.

Preferably, either one of R2 and R3 is hydrogen or an aliphatic group and the other is an aromatic group. A combination of hydrogen and a phenyl group, hydrogen and a naphthyl group, methyl and phenyl groups, or methyl and naphthyl groups is more preferred. Particularly preferred is a combination of methyl and phenyl groups.

The compound represented by the structural formula 1, when exposed to a radiation, generates amine having a structure of R1($-NH_2$)$_n$ or R1($-NH-NH_2$)$_n$.

In a particular aspect of the present invention, R1 is an organic group represented by the structural formula 2.

In the structural formula 2, R4 is an (m+n)-valent organic group, preferably an aliphatic, aromatic, polyurethane, polyether or polyester group, more preferably, an aromatic group.

If a molecular weight of R4 in the structural formula 2 is excessively low, the photosensitive amine generator shows the reduced compatibility with an amine-curable compound. On the other hand, if it is excessively high, the generated amine compound shows the reduced reactivity. Accordingly, R4 preferably has a molecular weight of 200-20,000, more preferably 400-10,000, further preferably 400-5,000.

In the structural formula 2, m is a positive integer of 1 or larger. In such a case, n is preferably 2 or larger.

If R5 in the structural formula 2 exists in plurality, such R5's may be identical to or different from each other. Preferably, R5 is at least one selected from the group consisting of isocyanate, (meth)acryloyl and vinyl groups.

The compound of the structural formula 1, if having a group represented by the structural formula 2, generates amine having a structure of (R5-)$_m$R4($-NH_2$)$_n$ or (R5-)$_m$R4($-NH-NH_2$)$_n$ upon exposure to a radiation.

Preferably, the photosensitive amine generator represented by the structural formula 1 comprises a product formed as a result of a reaction between an oxime compound and an isocyanate compound containing an isocyanate group bound to aromatic hydrocarbon. This product exhibits particularly good photodecomposability even without the assistance of a photosensitizer.

Any method can be utilized to obtain the photosensitive amine generator represented by the structural formula 1. The photosensitive amine generator can be obtained, for example, by charging a urethane prepolymer (or alternatively, a low-molecule-weight isocyanate compound) and an oxime compound in such a proportion that the number of moles of an isocyanate group in the urethane prepolymer is brought into agreement with that of a hydroxyl group in the oxime compound, and then reacting them with the optional addition of a catalyst such as a tin catalyst or tertiary amine.

In the case where R1 in the structural formula 1 is a (meth)acryloyl or vinyl group, the photosensitive amine generator can be obtained, for example, by reacting an oxime with a compound either having isocyanate and acryloyl groups or having isocyanate and vinyl groups, e.g., 2-methacryloyl-oxyethyl isocyanate or dimethylmethaneisopropenylbenzyl isocyanate; or by reacting hydroxyl- or carboxyl-containing (meth)acrylate with polyfunctional isocyanate and then reacting the remaining isocyanate groups with an oxime.

Examples of hydroxyl-containing (meth)acrylates include, but not limited to, 2-hydroxyethyl (meth)acrylate, 2-hydroxypropyl (meth)acrylate, 2-methacryloyloxyethyl acid phosphate, glycerin dimethacrylate, 2-hydroxy-3-acryloyloxy-propyl methacrylate and 2-(meth)acryloyloxyethyl-2-hydroxyethyl phthalate epoxy ester. Examples of carboxyl-containing (meth)acrylates include (meth)acrylic acid, 2-(meth)acryloyloxyethylsuccinic acid, 2-(meth)acryloyloxy-ethylhexahydrophthalic acid and 2-acryloyloxyethylphthalic acid.

If the photosensitive amine generator specified by the structural formula 1 is manufactured under such conditions that R5 in the structural formula 2 is an isocyanate group and (number of moles of an isocyanate group)/(number of moles of a hydroxyl group in the oxime) exceeds 1, a product is obtained in which a value of m in the structural formula 2 mostly exceeds 1. When such a product is exposed to a radiation, the generated amine reacts with the remaining isocyanate groups. This permits self-curing of the product. The occurrence of self-curing is increased particularly when R4 is an aromatic hydrocarbon group. Such a case is thus preferred.

Also, if (number of moles of an isocyanate group) □ (number of moles of a hydroxyl group in the oxime), the isocyanate group becomes larger in number than an amino group in the amine generated by irradiation. This permits the isocyanate group to undergo a curing reaction under the presence of a moisture or other form of water.

Accordingly, two-stage curing can be achieved by a reaction between the amine generated by irradiation and the isocyanate group and the subsequent moisture-cure reaction involving the isocyanate group.

In the present invention, the photosensitive amine generator may comprise a polymer or an oligomer made via copolymerization of a compound having a free-radically polymerizable group with a monomer having (meth)acryloyl and carbamoyloxyimino groups.

Examples of compounds having a free-radically polymerizable group include, but not limited to, (meth)acrylic acid; alkyl (meth)acrylate esters represented as by methyl (meth) acrylate ester, ethyl acrylate ester, n-propyl (meth)acrylate ester, isopropyl (meth)acrylate ester, n-butyl (meth)acrylate ester, sec-butyl (meth)acrylate ester, t-butyl (meth)acrylate ester, pentyl (meth)acrylate ester, hexyl (meth)acrylate ester, cyclohexyl (meth)acrylate ester, heptyl (meth)acrylate ester, n-octyl (meth)acrylate ester, isooctyl (meth)acrylate ester, 2-ethylhexyl (meth)acrylate ester, decyl (meth)acrylate, isononyl (meth)acrylate ester, hydroxyethyl (meth)acrylate ester, isomyristyl (meth)acrylate ester, isostearyl (meth)acrylate ester, stearyl (meth)acrylate ester, lauryl (meth) acrylate ester, glycidyl (meth)acrylate, 2-hydroxyethyl (meth)acrylate, n-butoxyethyl (meth)acrylate, phenoxyethyl (meth)acrylate, tetrahydrofurfuryl (meth)acrylate, benzyl (meth)acrylate, tribromophenyl (meth)acrylate, 2,3-dichloro-propyl (meth)acrylate, ε-(poly)caprolactone acrylate and tetrahydrofuranyl acrylate; styrene monomers represented as by α-methylstyrene, vinyltoluene, chlorostyrene, t-butyl-styrene and styrene; vinyl ether monomers represented as by methyl vinyl ether, ethyl vinyl ether and isobutyl vinyl ether; fumaric acid; maleic acid; itaconic acid; phthalic acid; monoalkyl esters and dialkyl esters of fumaric acid; monoalkyl esters and dialkyl esters of maleic acid; mono-alkyl esters and dialkyl esters of itaconic acid; monoalkyl esters and dialkyl esters of phthalic acid; aminoalkyl acrylate esters such as N,N-dimethylaminoethyl acrylate, N,N-diethylaminoethyl acrylate and N,t-butylaminoethyl acrylate; (meth)acrylonitrile; butadiene; isoprene; vinyl chloride; vinylidene chloride; vinyl acetate; vinyl ketone; N-vinyl pyrrolidone; vinyl pyridine; (meth)acrylamide; vinyl carbazole; divinyl benzene; urethane acrylates obtained as by a reaction between an isocyanate-containing compound and a (meth)acrylic monomer containing active hydrogen; epoxy ester compounds obtained as by a reaction of an epoxy-containing compound with acrylic acid or with a hydrogen-containing (meth)acrylic monomer; polyester acrylates; alkylene glycol mono(meth)acrylates, dialkylene glycol (meth)acrylates, polyalkylene glycol (meth)acrylates, alkylene glycol di(meth)acrylates and polyalkylene glycol di(meth)acrylates, which can be obtained by a reaction of alkylene glycol, such as ethylene glycol and propylene glycol, with acrylic acid; glycerin mono(meth)acrylates, glycerin di(meth)acrylates and glycerin tri(meth)acrylates; trimethylolalkane tri(meth)acrylates; acrylamides; silicon acryltate; polybutadiene acrylate; and the like.

One example of the monomer having (meth)acryloyl and carbamoyloxyimino groups is a compound represented by the strucutural formula 1 having the structural formula 2 in which R5 is a (meth)acryloyl group.

Copolymerization of the compound having a free-radically polymerizable group with the monomer having (meth) acryloyl and carbamoyloxyimino groups can be effected by any known conventional technique.

As stated above, the compound having a free-radically polymerizable group and the monomer having (meth)acryloyl and carbamoyloxyimino groups are copolymerized to provide a polymer. This allows easy control of compatibility thereof with the amine-curable compound by a suitable choice of the type of the copolymer compound having a free-radically polymerizable group. This also enables introduction of plural carbamoyloxyimino groups into a polymer molecule. As a result, a rate of photo-induced cure can be increased.

The type of the free-radical initiator is not particularly specified. Preferably, it initiates free-radical polymerization upon exposure to a radiation. Examples of such initiators include direct cleavage type initiators such as arylalkyl ketone, oxime ketone, acyl phosphine oxide, S-phenyl thiobenzoate and titanocene; hydrogen abstraction type initiators such as aromatic ketone, thioxanthone, benzyl and quinone derivatives and 3-ketocoumarin; composite type free-radical initiators such as organic peroxide/electron donative dye, bis-imidazole, onium salt/electron donative dye, N-phenylglycine/electron attractive dye, and N-phenylglycine/diphenyl iodonium salt/sensitizer; and the like.

The photosensitive amine generator of this invention, when used in combination with a photosensitizer, shows the improved photodecomposability.

Examples of such photosensitizers include triplet excitation energy transfer photosensitizers and electron transfer photosensitizers.

Specific examples thereof include acetophenones, benzophenone, Michler's ketone, benzil, benzoin, benzoin ether, benzyldimethylketal, benzoylbenzoate, α-acyloxime ester, tetramethylthiuram monosulfide, thioxanthone, aliphatic amine, aromatic-containing amine, nitrogen-containing ring systems such as piperidine, allylthiourea, O-tolylthiourea, sodium diethyl dithiophosphate, soluble salts of aromatic sulfinic acid, N,N-disubstituted-p-aminobenzonitrile compounds, tri-n-butylphosphine, N-nitrosohydroxylamine derivatives, oxazolidine compounds, tetrahydro-1,3-oxazine compounds, condensates of diamine and formaldehyde or acetoaldehyde, anthracene (or derivatives thereof), xanthine, cyanine dye porphyrins (or derivatives thereof) such as N-phenylglycine, phthalocyanine, naphthocyanine and thiocyanine, and the like.

The use of the photosensitive amine generator of the present invention in combination with the thioxanthone sensitizer, among those listed above, results in a marked improvement in photodecomposability. The thioxanthone sensitizer, as termed herein, encompasses thioxantone and substituted thioxanthones such as 2,4-diethylthioxanthone, 2-chlorothioxanthone, 2,4-diisopropylthioxanthone, 2,4-dimethylthioxanthone and isopropylthioxanthone.

A photodecomposability improving effect becomes notable particularly when the thioxanthone sensitizer is used in combination with a compound represented by the structural formula 2 wherein R4 is aliphatic hydrocarbon and R5 is an isocyanate group. The thioxanthone sensitizer also serves as a free-radical polymerization initiator.

The photosensitizer may be preferably incorporated in the amount of 1-100 parts by weight, more preferably 1-50 parts by weight, based on 100 parts by weight of the photosensitive amine generator. If the amount of the photosensitizer is below 1 part by weight, a sufficient sensitizing effect may not be obtained.

Examples of amine-curable compounds for use in the photocurable composition in accordance with the present invention include, but not particularly limited to, urethane prepolymers having a reactive isocyanate group; epoxy resins having an epoxy group; epoxy-containing oligomers; addition polymers of epoxy-containing oligomers; epoxy compounds such as epoxy-modified condensation polymers or epoxy-containing monomers; (meth)acryloyl-containing acrylic compounds; vinyl compounds having a vinyl group and compounds having a free-radically polymerizable double bond.

Among them, urethane prepolymers are preferred for use as the amine-curable compound in the present invention. These urethane prepolymers are reaction products obtainable from a reaction between a polyhydroxy compound and a polyisocyanate compound and having an isocyanate residue.

The polyhydroxy compound for use in the aforementioned reaction is not particularly specified in type. Those generally used in the manufacture of urethane compounds, such as polyether polyol, polyester polyol or polymer polyol, may preferably be used.

The above-listed polyhydroxy compounds may be used alone or in combination.

The polyether polyol is not particularly specified in type. Illustrative thereof is a polymer obtained via a ring-opening polymerization of alkylene oxide under the presence of a low-molecular-weight active hydrogen compound having two or more active hydrogen atoms.

Specific examples of low-molecular-weight active hydrogen compounds having two or more active hydrogen atoms include, diols such as bisphenol A, ethylene glycol, propylene glycol, butylene glycol and 1,6-haxanediol; triols such as glycerin and trimethylolpropane; amines such as ethylenediamine and butylenediamine; and the like.

The above-listed low-molecular-weight active hydrogen compounds having two or more active hydrogen atoms may be used alone or in combination.

Specific examples of alkylene oxides include ethylene oxide, propylene oxide, butylene oxide, amylene oxide, hexylene oxide, tetrahydrofuran and the like.

The above-listed alkylene oxides may be used alone or in combination.

The polyester polyol is not particularly specified in type. Examples thereof include, but not particularly limited to, polymers obtained via hydrating condensation of a polybasic acid, such as adipic acid, azelaic acid, sebacic acid, terephthalic acid, isophthalic acid or succinic acid, and a polyhydric alcohol such as bisphenol A, ethylene glycol, 1,2-propylene glycol, 1,4-butanediol, diethylene glycol, 1,6-hexane glycol or neopentyl glycol; polymers of lactones such as ε-caprolactone and α-methyl-ε-caprolactone; condensates of hydroxycarboxylic acid, such as castor oil or a reaction product of castor oil and ethylene glycol, and any of the above-listed polyhydric alcohols; and the like.

The above-listed polyester polyols may be used alone or in combination.

The polymer polyol is not particularly specified in type. Examples thereof include graft polymers obtained by grafting an ethylenically unsaturated compound, such as acrylonitrile, styrene or methyl (meth)acrylate, to any of the aforementioned polyether polyols and polyester polyols; 1,2-polybutadiene polyols, 1,4-polybutadiene polyol and hydrides thereof; and the like.

The above-listed polymer polyols may be used alone or in combination.

A weight average molecular weight of the polymer polyol is not particularly specified, but may preferably be in the approximate range of 100-50,000, more preferably in the approximate range of 500-5,000.

Examples of polyisocyanate compounds for use in the manufacture of urethane prepolymers include, but not limited to, 2,4-tolylene diisocyanate, phenylene diisocyanate, xylene diisocyanate, diphenylmethane-4,4'-diisocyanate (MDI), mixtures (crude MDI) of MDI and triphenylmethane triisocyanate or the like, 1,5-naphthylene diisocyanate, isophorone diisocyanate, dicyclohexylmethane diisocyanate, A ethylene diisocyanate, methylene diisocyanate, propylene diisocyanate, tetraethylene diisocyanate, triphenylmethane triisocyanate, hydrides thereof and the like. The use of MDI and crude MDI, among them, is preferred for their excellence in safety and reactivity.

The above-listed polyisocyanate compounds may be used alone or in combination.

A manufacturing method of the urethane prepolymer for use in the manufacture of the photo-curable composition in accordance with the present invention is not special. The desired urethane prepolymer can be obtained, for example, by mixing the polyhydroxy compound, and polyisocyanate compound such that an equivalent ratio (NCO/OH) of the isocyanate groups (NCO) of the polyisocyanate compound to the hydroxyl groups (OH) of the polyhydroxy compound comes within 1.2-15, preferably 3-12, and then reacting the mixture in a nitrogen stream at a temperature of about 80-100° C. for about 3-5 hours.

If the NCO/OH equivalent ratio falls below 1.2, the viscosity of the resulting urethane prepolymer may become excessively high to result in the difficulty to obtain an adhesive composition. On the other hand, if the NCO/OH equivalent ratio goes beyond 15, the resulting adhesive composition shows the increased tendency to foam during curing. This may cause reduction in cohesion of the cured product to result in the failure to obtain sufficient bond strength.

Examples of epoxy resins include, but not particularly limited to bisphenol A, bisphenol F, phenol-novolac, cresol-novolac, glycidyl ether and glycidyl amine type epoxy resins.

Examples of epoxy-containing oligomers include, but not particularly limited to, bisphenol A epoxy oligomers (such as EPICOAT 1001 and EPICOAT 1002, manufactured by Yuka-Shell Epoxy Co.).

Examples of epoxy-modified condensation polymers include, but not particularly limited to, glycidylated polyester, glycidylated polyurethane and glycidylated polyacrylic polymers.

Examples of epoxy-containing acrylic polymers include glycidylated polyacrylic polymers obtained, for example, by a method which comprises reacting a hydroxyl-containing acrylic polymer with epichlorohydrin or by a method which comprises copolymerizing glycidyl (meth)acrylate with a vinyl-containing comonomer.

Examples of (meth)acryloyl-containing acrylic compounds include, but not particularly limited to, (meth)acrylic acid; (meth)acrylate esters such as methyl (meth)acrylate ester, ethyl (meth)acrylate ester, n-propyl (meth)acrylate ester, isopropyl (meth)acrylate ester, n-butyl (meth)acrylate ester, sec-butyl (meth)acrylate ester, t-butyl (meth)acrylate ester, pentyl (meth)acrylate ester, hexyl (meth)acrylate ester, cyclohexyl (meth)acrylate ester, heptyl (meth)acrylate ester, n-octyl (meth)acrylate ester, n-isooctyl (meth)acrylate ester, 2-ethylhexyl (meth)acrylate ester, decyl (meth)acrylate ester, isononyl (meth)acrylate ester, lauryl (meth)acrylate ester, isomyristyl (meth)acrylate ester, stearyl (meth)acrylate ester, isostearyl (meth)acrylate ester, hydroxyethyl (meth)acrylate ester, n-butoxyethyl (meth)acrylate ester, phenoxyethyl (meth)acrylate ester, tetrahydrofurfuryl (meth)acrylate ester, benzyl (meth)acrylate ester, tribromophenyl (meth)acrylate ester, 2,3-dichloropropyl (meth)acrylate ester, tetrahydrofuranyl (meth)acrylate ester and ε-(poly)caprolactone acrylate; urethane acrylates obtained as by a reaction between an isocyanate-containing compound and an active hydrogen-containing (meth)acrylic monomer; epoxy ester compounds obtained as by a reaction between an epoxy-containing compound and acrylic acid or hydroxyl-containing (meth)acrylic monomer; polyester acrylates; alkylene glycol mono(meth)acrylates obtained as by a reaction of alkylene glycol, such as ethylene glycol or propylene glycol, with (meth)acrylic acid; alkylene glycol di(meth)acrylates such as ethylene glycol dimethacrylate, 1,4-butanediol dimethacrylate, 1,6-hexanediol dimethacrylate and 1,9-nonanediol dimethacrylate; polyalkylene glycol mono(meth)acylates; alkylene glycol di(meth)acrylates; dialkylene glycol mono(meth)acrylates such as diethylene glycol monomethacrylate; dialkylene glycol di(meth)acrylates; polyalkylene glycol di(meth)acrylates; polyol (meth)acrylates such as glycerin mono(meth)acrylate, glycerin di(meth)acrylate, glycerin tri(meth)acrylate, trimethylolpropane tri(meth)acrylate, ditrimethylolpropane tetraacrylate, pentaerythritol triacrylate, pentaerythritol tetraacrylate, dipentaerythritol pentaacrylate and dipentaerythritol hexaacrylate; (meth)acrylamides; (meth)acrylonitrile; aminoalkyl acrylate esters such as N,N-dimethylaminoethyl acrylate ester, N,N-diethylaminoethyl acrylate ester and N-t-butylaminoethyl acrylate ester; silicone acrylates; polybutadiene acrylates; 2-hydroxy-3-acryloyloxypropyl methacrylate, ethylene oxide-added bisphenol A dimethacrylate, PO-modified trimethylolpropane trimethacrylate, EO-modified trimethylolpropane trimethacrylate and the like.

Examples of vinyl-containing vinyl compounds include, but not particularly limited to, vinyl chloride, vinylidene chloride, vinyl acetate, vinyl ketone, methyl vinyl ether, ethyl vinyl ether, isobutyl vinyl ether, N-vinylpyrrolidone, vinylpyridine, vinylcarbazole, styrene, vinyltoluene, divinylbenzene, α-methylstyrene, chlorostyrene, t-butyl styrene and the like.

Examples of compounds having a free-radically polymerizable double bond include, but not particularly limited to, butadiene, isoprene, fumaric acid and its dialkyl ester, maleic acid and its monoalkyl ester and dialkyl ester, itaconic acid and its monoalkyl ester and dialkyl ester, phthalic acid and its monoalkyl ester and dialkyl ester, and the like.

The photocurable composition in accordance with the fourth invention contains the aforementioned amine-curable compound (hereinafter referred to as compound A) and photosensitive amine generator B.

The photosensitive amine generator B for use in the fourth invention is a compound having a carbamoyloxyimino group.

The compound represented by the structural formula 1, as described above, is suitable for use as the compound having a carbamoyloxyimino group.

The photocurable composition in accordance with the present invention has high storage stability since the functional group of the amine-curable compound A remains unreacted before exposure to a radiation.

Upon exposure to a radiation, it generates amine which then starts to react with the functional group of the amine-curable compound A. Curing of the amine-curable compound A does not complete immediately. This affords us a time to combine adherends after the composition has been exposed to a radiation. During this time period, the amine generated by irradiation continues to react with the functional group of the amine-curable compound A. Since the reaction between the amine and the functional group proceeds in a relatively speedy fashion, the composition exhibits high initial bond strength and heat resistance in a short time after it has combined the adherends.

In the case where the amine-curable compound A is a urethane prepolymer, if the number of moles of amino groups of the generated amine is smaller than that of isocyanate groups of the urethane prepolymer, curing can be caused to complete by a moisture.

Preferred for use as the photosensitive amine generator B is a homopolymer of a monomer having a (meth)acryloyl group and a carbamoyloxyimino group, or alternatively, a copolymer obtained via polymerization of a compound having a free-radically polymerizable group with a monomer having a (meth)acryloyl group and a carbamoyloxyimino group. Here, the (co)polymer is intended to encompass oligomers.

The compound having a free-radically polymerizable group has been previously illustrated in the description of the compound having the structural formula 1.

The monomer having a (meth)acryloyl group and a carbamoyloxyimino group is represented by the following structural formula 3:

[Structural Formula 3]

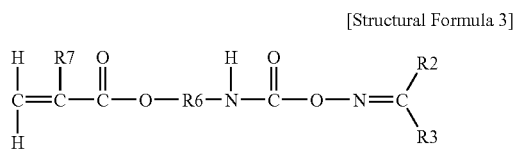

In the structural formula 3, R7 is hydrogen or a methyl group, R2 and R3 are similar to the case of the structural formula 1, and R6 is a divalent organic group such as alkylene, phenylene, xylylene, polyether or polyester.

Copolymerization of the compound having a free-radically polymerizable group with the monomer having a (meth)acryloyl group and a carbamoyloxyimino group can be carried out by a conventional method.

The polymer obtained via the above copolymerization, when exposed to a radiation, generates amine in a manner similar to the compound having a carbamoyloxyimino group.

The resulting amine starts to react with the functional group of the amine-curable compound A. Also in this case, when adherends are combined together after the composition is exposed to a radiation, amine generated by irradiation continues to react with the functional group of the amine-curable compound A. Accordingly, the composition exhibits high initial bond strength and heat resistance in a relatively short time after it has combined the adherends.

In the case where the amine-curable compound A is a urethane prepolymer, if the number of moles of amino groups of the generated amine is smaller than that of isocyanate groups of the urethane prepolymer, curing can be caused to complete by a moisture.

As stated above, the compound having a free-radically polymerizable group and the monomer having a (meth)acryloyl group and a carbamoyloxyimino group are copolymerized to provide a polymer. This allows suitable control of the type and molecular weight of the copolymerizing compound having a free-radically polymerizable group, permits easy control of compatibility thereof with the amine-curable compound, and enables introduction of plural carbamoyloxyimino groups into a polymer molecule so that a rate of photo-induced cure can be increased.

Also, a reaction of isocyanate groups of a urethane prepolymer with an oxime compound results in obtaining a urethane prepolymer having a carbamoyloxyimino group. The use of this latter urethane prepolymer as the compound B having a carbamoyloxyimino group increases compatibility thereof with the amine-curable compound and also enables introduction of plural carbamoyloxyimino groups into a polymer molecule so that a rate of photo-induced cure can be increased.

A compound having a carbamoyloxyimino group and another functional group selected from isocyanate, epoxy and free-radically polymerizable groups is preferred because such a compound itself cures as a result of a reaction of amine generated by irradiation with the functional group such as an isocyanate, epoxy or free-radically polymerizable group.

The compound having isocyanate and carbamoyloxyimino groups may be illustrated by a compound having an isocyanate group located in an R1 portion of the strucutral formula 1 and can be synthesized by reacting an isocyanate-containing compound, such as a urethane prepolymer or an isocyanate compound, with an oxime. For this reaction, a tin compound and tertiary amine can be suitably used as a catalyst.

If (number of moles of isocyanate groups)/(number of moles of hydroxyl groups of the oxime) in the above reaction exceeds 1, the resulting compound mostly has excessive isocyanate groups.

Particularly when the number of moles of isocyanate groups exceeds that of hydroxyl groups of the oxime, more isocyanate groups exist than the amino groups of the amine generated by irradiation, so that a curing reaction of the isocyanate groups under the presence of a moisture or other form of water can be fairly expected.

The compound having a free-radically polymerizable group and a carbamoyloxyimino group may be a compound having a (meth)acryloyl group, a vinyl group, an unsaturated double bond or the like located in a portion of the structural formula 1, for example.

The fifth invention of this application provides a photocurable composition which contains an amine-curable compound A, a photosensitive amine generator B having a free-radically polymerizable group and a carbamoyloxyimino group, and a free-radical photoinitiator C. The amine-curable compound A is similar to those described in the first through fourth inventions.

When the photocurable composition in accordance with the fifth invention is irradiated, the photoinitiator C is initially activated to generate a free radical. The generated free radical induces free-radical polymerization of the free-radically polymerizable group to provide a polymer. The irradiation further induces generation of amine by the same mechanism as described in the first through fourth inventions. This amine and the functional group of the amine-curable compound A initiate a reaction to impart high initial bond strength and heat resistance in a short time period as analogously to the first through fourth inventions.

Also in the fifth invention, the amine-curable compound A may comprise a urethane prepolymer as analogously to the sixth and seventh inventions. In such a case, if the number of moles of the amino groups of the generated amine is smaller than that of the isocyanate groups of the urethane prepolymer, curing can be caused to complete by a moisture.

In the photocurable composition in accordance with the fifth invention, the photosensitive amine generator B is initially supplied in the monomeric form and then rendered into a polymer by the above-described free-radical photo-polymerization. This lowers an initial viscosity and accordingly increases spreadability of the photocurable composition. Also in the fifth invention, the compound having a free-radically polymerizable group, as preferably used in the first invention, may be added, if necessary.

The useful free-radical photoinitiator C was described ealier. As also described earlier, in addition to being useful as a photosensitizer, the thioxanthone sensitizer can also serve as a free-radical initiator.

The aforementioned photosensitizer may preferably be incorporated in the photocurable composition in accordance with the fifth invention, as analogous to the first through fourth inventions.

(Gel Fraction after Irradiation)

In order that the photocurable composition in accordance with the present invention exhibits sufficient heat resistance immediately after irradiation, it is desired that the composition shows a gel fraction in the range of 0-60 weight %, more preferably in the range of 5-50 weight %, immediately after irradiation. When necessary, heating may follow the irradiation to promote a curing reaction.

(Additives)

Besides the essential components, the photocurable composition in accordance with the present invention may further contain one or more of various additives including silane coupling agents serving as adhesion improvers, agents, fillers, thixotropic agents, coloring agents, plasticizers (softeners), stabilizers, antioxidants, UV absorbers and organic solvents.

Examples of silane coupling agents include, but not particularly limited to, amino alkoxy silanes such as γ-aminopropyl trimethoxy silane and N-β(aminoethyl)-γ-aminopropyl trimethoxy silane; mercapto alkoxy silanes such as γ-mercaptopropyl trimethoxy silane; epoxy alkoxy silanes such as γ-glycidoxypropyl trimethoxy silane and 3,4-epoxy-cyclohexylethyl trimethoxy silane; vinyl silanes such as vinyl tris(β-methoxyethoxy) silane and vinyl triethoxy silane; and silane compounds having an isocyanate group and an alkoxysilyl group such as γ-isocyanatepropyl triethoxy silane. One or more of these may be suitably used.

Examples of fillers include, but not particularly limited to, mica powder, calcium carbonate, surface-treated calcium carbonate, carbon black, talc, titanium oxide, rubber powder, organic balloon, inorganic balloon and wollastonite. One or more of these may be suitably used.

The shape of the filler is not particularly limited and may be powdery, flaky, spherical, blocky or needle-like.

Examples of thixotropic agents include, but not particularly limited to, colloidal silica, hydrogenated castor oil and organic bentonite. One or more of these may be suitably used.

Examples of plasticizers include, but not particularly limited to, dioctyl phthalate (DOP), dibutyl phthalate, dilauryl phthalate, dioctyl adipate, diisodecyl adipate, tributyl phosphate, trioctyl phosphate, propylene glycol adipate polyester, butylene glycol adipate polyester, epoxidized soy bean oil, hydrogenated paraffin and liquid paraffin. One or more of these may be suitably used.

Examples of stabilizers include, but not particularly limited to, benzotriazole UV absorbers such as TINUVIN 327 (product of Ciba Geigy Co.), hindered phenol antioxidants such as IRGANOX 1010 (product of Ciba Geigy Co.), hindered amine light stabilizers and benzoate UV stabilizers. One or more of these may be suitably used.

Examples of organic solvents include, but not particularly limited to, synthetic isoparaffin solvents having flash points of 40° C. and higher. One or more of these may be suitably used.

The photocurable composition in accordance with the invention of this application can be suitably used as a photoreactive adhesive. In a method for joining members using a photoreactive adhesive, in accordance with the present invention, a photoreactive adhesive composition is exposed to a radiation when combining the members to be joined by using the photoreactive adhesive. As used herein, when combining the members means that the photoreactive adhesive composition may be exposed to a radiation before combination thereof, or alternatively, after combination thereof. That is, the method may comprise coating at least one of the members with the photoreactive adhesive composition, exposing the coated composition to a radiation and combining the members with each other. Alternatively, the method may comprise combining the members with each other by the photoreactive adhesive composition and then exposing the composition to a radiation. In either case, irradiation induces generation of amine and then a reaction between the generated amine and an amine-curable group of the amine-curable compound is allowed to go proceed. As a result, the composition exhibits improved initial bond strength and heat resistance.

In the case where at least one of the members has the property of transmitting a radiation, combination thereof may precede the irradiation since such a configuration assures exposure of the composition, through the one member, to a radiation.

The photosensitive amine generator in accordance with the present invention exhibits superior photodecomposable property and generates amine at high efficiency when exposed to a radiation. When used in combination with an amine-curable compound such as a urethane prepolymer or an epoxy compound, it constitutes a photocurable composition suitable for use as a photocuable agent, such as an adhesive, pressure-sensitive adhesive, paint, coating material, resist, sealing material or ink.

EXAMPLE 1

0.1 mol of acetophenone oxime dissolved in 100 ml of tetrahydrofuran (THF) was added to 0.05 mol of hexamethylene diisocyanate. The mixture was reacted with stirring under dry nitrogen atmosphere at 50° C. for 4 hours. Subsequent volatilization of tetrahydrofuran from a reaction liquid resulted in obtaining a white-colored solid. This white solid was dissolved in methyl ethyl ketone at 80° C. and then purified via recrystallization to prepare a photosensitive amine generator (hereinafter referred to as compound 1).

EXAMPLE 2

0.1 mol of acetophenone oxime dissolved in 100 ml of tetrahydrofuran was added to 0.05 mol of tolylene diisocyanate. The mixture was reacted with stirring under dry nitrogen atmosphere at 50° C. for 4 hours. Subsequent volatilization of tetrahydrofuran from a reaction liquid resulted in obtaining a white-colored solid. This white solid was dissolved in methyl ethyl ketone at 80° C. and then purified via recrystallization to prepare a photosensitive amine generator (hereinafter referred to as compound 2).

EXAMPLE 3

0.15 mol of acetophenone oxime dissolved in 100 ml of tetrahydrofuran (THF) was added to 0.05 mol of TMP (trimethylolpropane)-modified hexamethylene diisocyanate (SUMIDULE available from Sumitomo-Bayer Urethane Co., Ltd) The mixture was reacted with stirring under dry nitrogen atmosphere at 50° C. for 4 hours. Subsequent volatilization of tetrahydrofuran from a reaction liquid resulted in obtaining an orange-colored liquid. Then, ethyl acetate was added to this orange liquid. The resulting mixture was subjected to shaking, left to stand overnight at 5° C. to remove a supernatant ethyl acetate layer and then purified by volatilizing the remaining solvent in a vacuum dryer. As a result, a photosensitive amine generator (hereinafter referred to as compound 3) was prepared.

EXAMPLE 4

0.05 mol of acetophenone oxime dissolved in 100 ml of tetrahydrofuran was added to 0.05 mol 2-methacryloyloxyethyl isocyanate (product of Showa Denko K.K.). The mixture was reacted with stirring under dry nitrogen atmosphere at 50° C. for 4 hours. Subsequent volatilization of tetrahydrofuran from a reaction liquid resulted in the preparation of a liquid-form photosensitive amine generator (hereinafter referred to as compound 4).

EXAMPLE 5

Polypropylene glycol having an average molecular weight of 700 (MN-300 manufactured by Mitsui Chemicals, Inc.) and hexamethylene diisocyanate were mixed such that the NCO/OH ratio was brought to 1.9, and then reacted at 80° C. for 5 hours. 10 parts by weight of acetophenone oxime was then added to 100 parts by weight of the product obtained. The mixture was reacted with stirring under dry nitrogen atmosphere at 50° C. for 4 hours to prepare a photosensitive amine generator (hereinafter referred to as compound 5).

EXAMPLE 6

80 parts by weight of ethyl acrylate, 20 parts by weight of the compound 4 obtained in Example 4 and 200 parts by weight of dewatered ethyl acetate were copolymerized at the boiling point, using a thermally-activated free-radical initiator (PERHEXA TMH manufactured by NOF Corp.), to prepare a photosensitive amine generator (hereinafter referred to as compound 6).

COMPARATIVE EXAMPLE 1

0.1 mol of o-nitrobenzyl alcohol dissolved in 100 ml of tetrahydrofuran was added to 0.05 mol of hexamethylene diisocyanate. The mixture was reacted with stirring under dry nitrogen atmosphere at 50° C. for 4 hours. Subsequent volatilization of tetrahydrofuran from a reaction liquid resulted in obtaining a white-colored solid. This white solid was purified by washing it with methyl ethyl ketone (the resulting product is hereinafter referred to as compound A).

COMPARATIVE EXAMPLE 2

0.1 mol of o-nitrobenzyl alcohol dissolved in 100 ml of tetrahydrofuran was added to 0.05 mol tolylene diisocyanate. The mixture was reacted with stirring under dry nitrogen atmosphere at 50° C. for 4 hours. Subsequent volatilization of tetrahydrofuran from a reaction liquid resulted in obtaining a white-colored solid. This white solid was purified by washing it with methyl ethyl ketone (the resulting product is hereinafter referred to as compound B).

(Preparation of Amine-Curable Compound)

Hexamethylene diisocyanate was added to 100 parts by weight of polyether triol comprised of trimethylolpropane and propylene oxide and having a weight average molecular weight of 4,000 (product of Asahi Denka Kogyo Co., Ltd., product name ADEKA POLYETHER T-4000) and 100 parts by weight of polypropylene oxide (weight average molecular weight of 6,000), so that the NCO/OH equivalent ratio was brought to 1.9. The mixture was reacted at 80° C. for 5 hours to obtain a urethane prepolymer (1).

(Solubility Evaluation)

For the compounds 1-6, A and B, the change between infrared absorption spectrum (hereinafter abbreviated as IR spectrum) of each compound prior to and subsequent to the reaction, particularly attributed to the NCO, NHC=O or C=O bond, were observed using a Perkin-Elmer infrared absorption spectrometer. In addition, the compounds 1-6, A and B were evaluated for solubility in tetrahydrofuran and compatibility with the urethane prepolymer (1) or the epoxy resin (EPICOAT 828). The evaluation results are given in Table 1.

Figure 2:
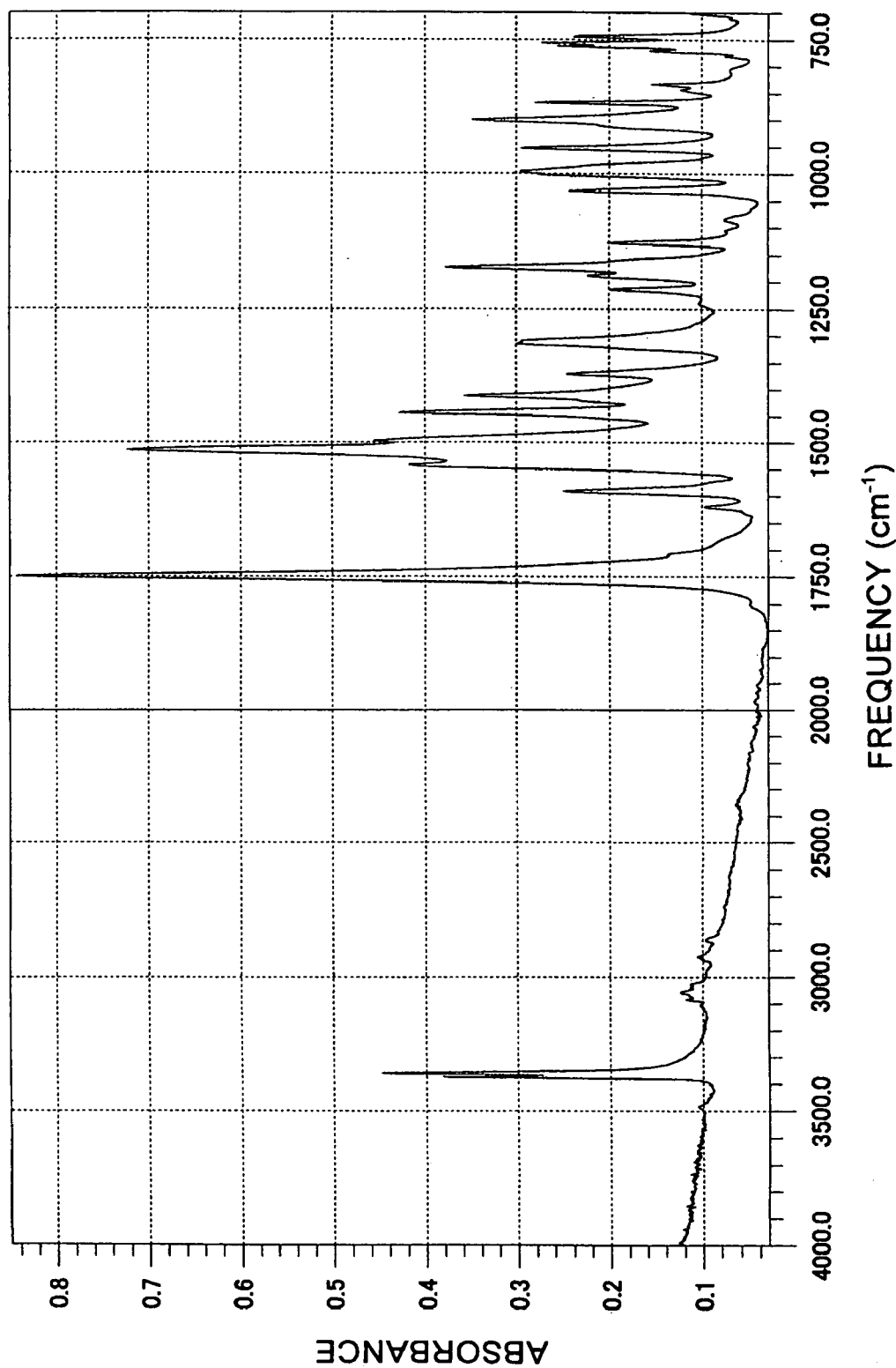
FIG. 2 shows an infrared absorption spectrum of the compound 2 as synthesized in Example 2.
Figure 3:
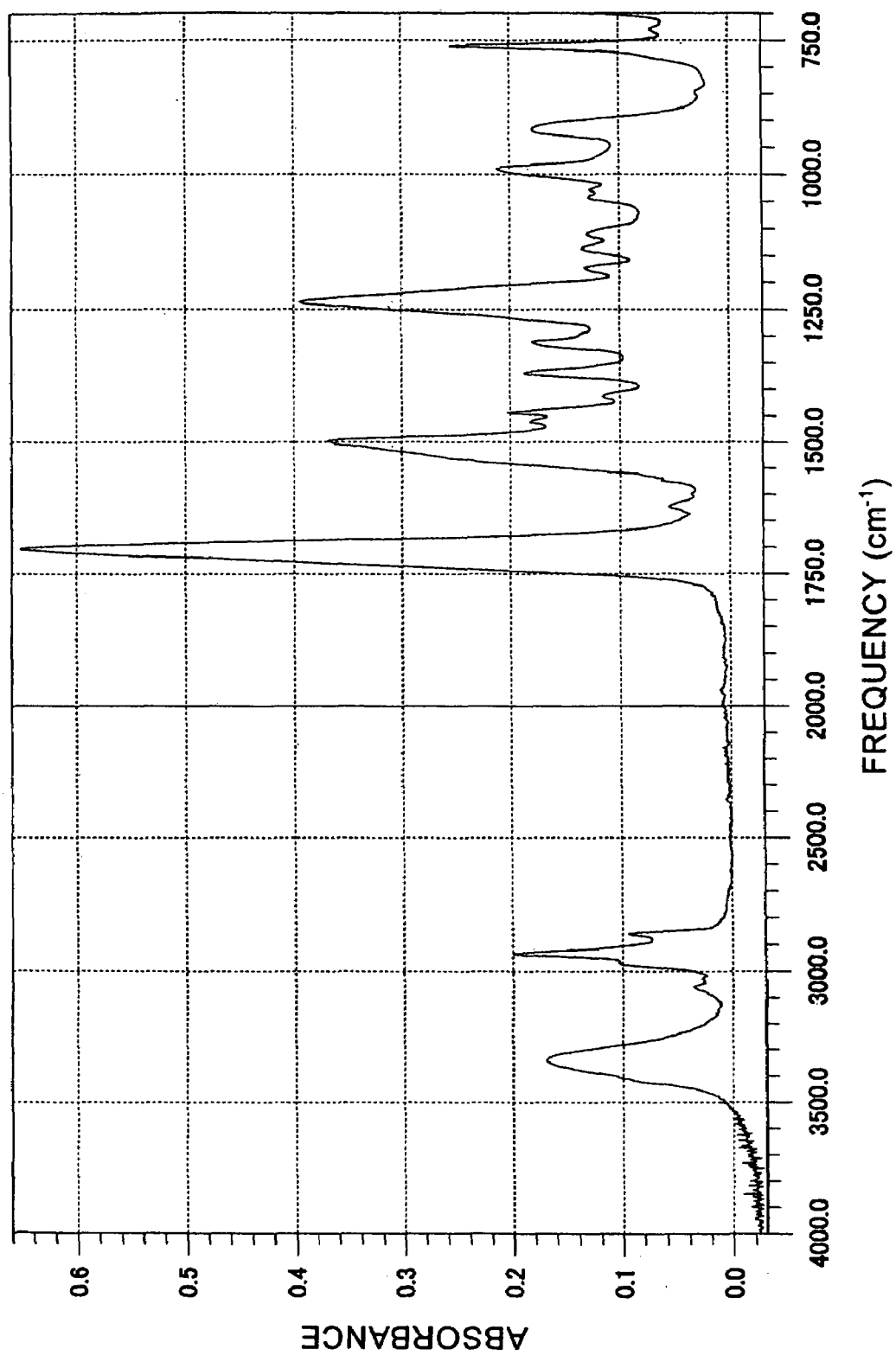
FIG. 3 shows an infrared absorption spectrum of the compound 3 as synthesized in Example 3.
Figure 4:
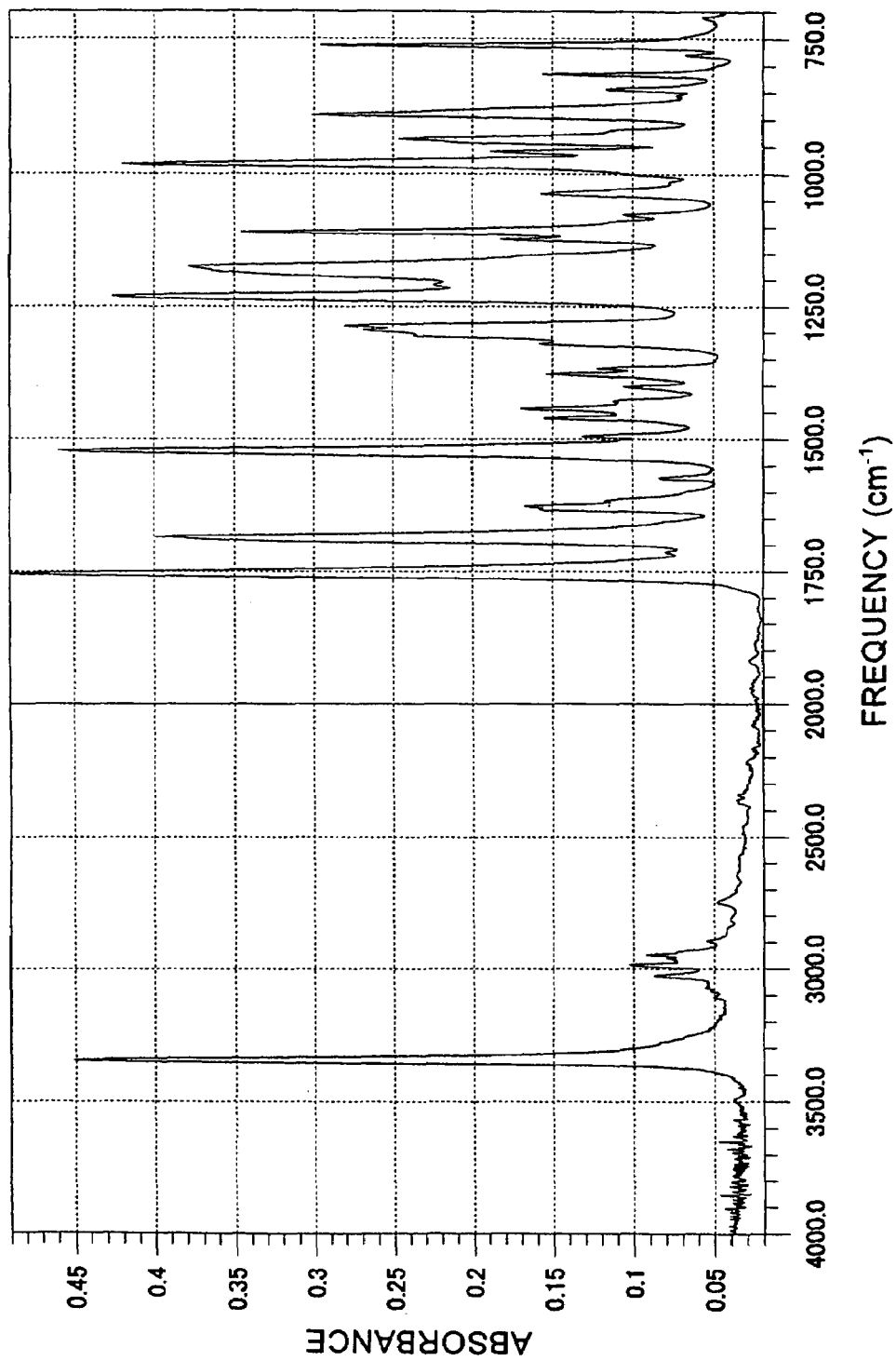
FIG. 4 shows an infrared absorption spectrum of the compound 4 as synthesized in Example 4.

FIGS. 1-4 show the respective IR spectra of the compounds 1-4.

In the evaluation of solubility and compatibility, 100 parts by weight of tetrahydrofuran, urethane prepolymer (1) or epoxy resin was added to and then mixed under agitation with 1 part by weight of each test specimen (each of the compounds 1-6, A and B) to observe their solubility characteristics. Evaluation was made by three ranks, i.e., by O if the composition dissolved completely and provided a clear mixture, by ▲ if it almost dissolved but provided a slightly cloudy mixture and by X if it little dissolved.

turing Co., Ltd.) for 1 minute. An infrared absorption spectrum of each sample was obtained, and a peak absorbance of the urethane bond (NHC=O) appearing near 1710 cm$^{-1}$ was determined (the determined value was designated as E2).

Further, the same sample as above was exposed to a radiation at 50 mW/cm$^2$ using an ultrahigh-pressure mercury lamp (JET LIGHT-2300, manufactured by ORC manufacturing Co., Ltd.) for 4 minutes. Thereafter, an infrared absorption spectrum of each sample was obtained, and a peak absorbance of the urethane bond (NHC=O) appearing near 1710 cm$^{-1}$ was determined (the determined value was designated as E3).

Percentage decompositions 1 and 2 were defined by percentages of values calculated from (E1-E2)/E1 and (E1-E3)/E1, respectively, using the values obtained for E1, E2 and E3, and were measured for the compounds 2 having a carbamoyloxyimino group and the compound B excluding a carbamoyloxyimino group. The measurement results are given in Table 2.

TABLE 1

| | Item | Example 1 | 2 | 3 | 4 | 5 | 6 | Comparative Example 1 | 2 |
|---|---|---|---|---|---|---|---|---|---|
| IR Spectral Position (cm$^{-1}$) | C=O | 1500 | 1531 | 1510 | 1500 | 1510 | 1520 | 1520 | 1550 |
| | NHC=O | 1730 | 1748 | 1710 | 1720 | 1720 | 1710 | 1699 | 1684 |
| | | | | | | | | | 1710 |
| | NCO | Absent | Absent | Absent | Absent | Absent | Absent | Absent | Absent |
| Solubility | THF | O | O | O | O | O | O | ▲ | ▲ |
| | Prepolymer | X | X | O | O | O | O | X | X |
| | Epoxy Resin | X | X | O | O | O | O | X | X |

In the IR spectral measurement results shown in Table 1, an absorption peak due to the isocyanate group (NCO) disappears while a peak due to the urethane bond (NHC=O) appears. This ascertains production of the compounds 1-6.

It is found from Table 1 that the compounds 1-6 having a carbamoyloxyimino group exhibit higher solubility to tetrahydrofuran than the compounds A and B. It can also be understood from comparison of the compounds 1 and 2 to the compounds 5 and 6 that the increase of a molecular weight of the R1 group in the structural formula 1 to certain levels results in the improved solubilities to the urethane prepolymer (2) and the epoxy resin.

(Evaluation of Photodecomposability)

As shown in Table 2, each of the compound 2 and the compound B was dissolved in tetrahydrofuran, coated on a potassium bromide plate and then dried to provide a sample. An infrared absorption spectrum of each sample was obtained, and a peak absorbance of the urethane bond (NHC=O) appearing near 1710 cm$^{-1}$ was determined using an IR spectrophotometer (the determined value was designated as E1).

Next, the same sample as above was exposed to a radiation at 50 mW/cm$^2$ using an ultrahigh-pressure mercury lamp (JET LIGHT-2300, manufactured by ORC manufac-

TABLE 2

| | Compound 2 | Compound B |
|---|---|---|
| Percentage Decomposition 1 (%) | 40 | 25 |
| Percentage Decomposition 2 (%) | 70 | 50 |

As can be clearly understood from Table 2, the compound 2 having a carbamoyloxyimino group when irradiated shows the higher tendency to generate amine.

SYNTHESIS EXAMPLE 1

Preparation of Urethane Prepolymer

Diphenylmethane-4,4'-diisocyanate (product of Nippon Polyurethane Industry Co., Ltd., product name: MILIONATE MT) was added to 100 parts by weight of polyether triol comprised of trimethylolpropane and propylene oxide and having a weight average molecular weight of 4,000 (product of Asahi Denka Kogyo Co., Ltd., product name: ADEKAPOLYETHER T-4000) and 100 parts by weight of polypropylene oxide (weight average molecular weight of 6,000), so that the NCO/OH equivalent ratio was brought to 1.9. The mixture was reacted at 80° C. for 5 hours to obtain a urethane prepolymer (2).

SYNTHESIS EXAMPLE 2

Synthesis of Carbamoyloxyimino-Containing Compound B 0.02 mol of hexamethylene diisocyanate, together with 0.04 mol of acetophenone oxime, were dissolved in 50 ml tetrahydrofuran (THF). The mixture was stirred under nitrogen atmosphere at 60° C. for 5 hours, left to stand at room temperature for 5 hours and then filtered to collect a white crystal which was subsequently dried in a vacuum drying oven to vaporize THF. The resulting compound was designated as compound 7.

SYNTHESIS EXAMPLE 3

Synthesis of a Polymer from Copolymerization of a Compound Having a Free-Radically Polymerizable Group and a Monomer Having an Acryloyl Group and a Carbamoyloxyimino Group 5 mmol of the compound 4 obtained in the Example 4 and 10 mmol of butyl acrylate were dissolved in 10 ml THF. After addition of 60 mg of 2,2'-azobisisobutyronitril, the resulting mixture was polymerized under nitrogen atmosphere at 60° C. for 5 hours to obtain a polymer solution. This polymer solution was introduced into a vacuum drying oven to remove benzene to thereby obtain a polymer. This polymer was designated as polymer 1.

EXAMPLE 7

10 parts by weight of the compound 7 and 1 part by weight of benzophenone were added to 100 parts by weight of the above-obtained urethane prepolymer (2). The mixture was stirred under a dry condition at 60° C. to homogeneity to obtain a photoreactive adhesive composition.

EXAMPLE 8

5 parts by weight of the compound 4 obtained in the preceding Example 4, 5 parts by weight of urethane acrylate (product of Kyoei-Sha Chemical, Co., Ltd., product number: AH-600) and 1 part by weight of benzophenone were added to 100 parts by weight of the above-obtained urethane prepolymer (2). The mixture was stirred under a dry condition at 60° C. to homogeneity to obtain a photoreactive adhesive composition.

EXAMPLE 9

10 parts by weight of the polymer 1 and 1 part by weight of benzophenone were added to 100 parts by weight of the above-obtained urethane prepolymer (2). The mixture was stirred under a dry condition at 60° C. to homogeneity to obtain a photoreactive adhesive composition.

COMPARATIVE EXAMPLE 3

The above-obtained urethane prepolymer (2) was used alone as a comparative example.

(Evaluation of Examples 7-9 and Comparative Example 3)

The following procedures were utilized to evaluate (1) bond strength, (2) heat resistance and (3) gel fraction for the adhesive compositions obtained in the preceding Examples and Comparative Example. The results are listed in the following Table 3.

(1) Bond Strength

Under a 23° C. atmosphere, each of the above-obtained one-part photoreactive adhesive compositions was coated on a 3 cm×10 cm area of a polished stainless steel plate (SUS plate)(3 cm×10 cm×0.2 cm, 45 g) to a thickness of 50 μm. The coated composition was then exposed to a radiation at 40 mW/cm$^2$ using an ultrahigh-pressure mercury lamp (JET LIGHT-2300, manufactured by ORC manufacturing Co., Ltd.) for 3 minutes. Thereafter, a corona-treated PET film was laminated thereon to provide a test piece.

The test piece was left to stand at room temperature for 30 minutes and then subjected to 180° peel adhesion measurement at a pulling rate of 50 mm/min to determine an initial bond strength.

Also, the test piece was aged at 23° C. for 7 days and then subjected to tensile peel adhesion measurement at a pulling rate of 50 mm/min to determine a bond strength after cure.

(2) Heat Resistance

Under a 23° C. atmosphere, each of the above-obtained one-part photoreactive adhesive compositions was coated onto a polished stainless steel plate (SUS plate) to a thickness of 100 μm. Thereafter, the coated composition was exposed to a radiation at 40 mW/cm$^2$ using a high-pressure mercury lamp (JET LIGHT-2300, manufactured by ORC manufacturing Co., Ltd.) for 3 minutes and then laminated with a corona-treated PET film. The corona-treated PET film was subsequently fixed so as to suspend the laminate vertically in a 80° C. oven, and the downward movement of the SUS plate was measured.

(3) Gel Fraction

Under a 23° C. atmosphere, each of the above-obtained one-part photoreactive adhesive compositions was coated onto a release-treated PET film to a thickness of 100 μm. The coated composition was exposed to a radiation at 40 mW/cm$^2$ using an ultrahigh-pressure mercury lamp (JET LIGHT-2300, manufactured by ORC manufacturing Co., Ltd.) for 3 minutes and then dissolved in tetrahydrofuran. A gel fraction (% by weight) was determined by taking the insoluble residue as a gel.

TABLE 3

|  | Ex.7 | Ex.8 | Ex.9 | Comp. Ex. 3 |
| --- | --- | --- | --- | --- |
| Initial Bond Strength (N/cm) | 4.9 | 4.9 | 4.9 | 0 |
| Bond Strength After Cure (N/cm) | 14.7 | 14.7 | 14.7 | 12.7 |
| Heat Resistance (80□) | No Downward Movement | No Downward Movement | No Downward Movement | Dropped After 30 sec. |
| Gel Fraction (wt. %) | 5 | 10 | 10 | 0 |

EXAMPLES 10-14 AND COMPARATIVE EXAMPLES 4 AND 5

The composition 1-3, 5 or 6 and 2-diethylthioxanthone (product of Nippon Kayaku Co., Ltd., product name: DETX-S) at the proportion specified in Table 4, based on 100 parts by weight of the urethane prepolymer (1), were mixed and stirred under a dry condition to homogeneity. As a result, photoreactive adhesive compositions of Examples 10-14 were obtained.

The compounds A and B were used in Comparative Examples 4 and 5.

Each of the above-obtained photoreactive adhesive compositions was coated onto a release-treated PET film to a film thickness of 50 μm. The coated film was exposed to a radiation at 50 mW/cm² using an ultrahigh-pressure mercury lamp (JET LIGHT-2300", manufactured by ORC manufacturing Co., Ltd.) for 1 minute.

Under a 23° C. atmosphere, the irradiated coating film comprising the photoreactive adhesive composition was then interposed between two polished stainless steel plates (3 cm×10 cm×0.2 cm) which were subsequently pressed against each other and combined together.

EXAMPLES 15 AND 16 AND COMPARATIVE EXAMPLES 6 AND 7

The composition 4,2-diethylthioxanthone (product of Nippon Kayaku Co., Ltd., product name: DETX-S) and urethane acrylate (product of Kyoei-Sha Chemical Co., Ltd., product number: AH-600) at the proportions specified in Table 5, based on 100 parts by weight of the urethane prepolymer (1), were mixed and stirred under a dry condition to homogeneity. As a result, photoreactive adhesive compositions were obtained. 2-diethylthioxanthone also serves as a free-radical photoinitiator for the compound 4.

The compound A was used in Comparative Examples 6 and 7.

Each of the above-obtained photoreactive adhesive compositions was coated onto a release-treated PET film to a film thickness of 50 μm. The coated film was exposed to a radiation at 50 mW/cm² using an ultrahigh-pressure mercury lamp (JET LIGHT-2300", manufactured by ORC manufacturing Co., Ltd.) for 1 minute.

Under a 23° C. atmosphere, the irradiated coating film comprising the photoreactive adhesive composition was then placed on a polished stainless steel plate (SUS plate)(3 cm×10 cm×0.2 cm) to cover an entire surface thereof. Another polished but differently-sized stainless steel plate was placed to sandwich the coating film between the two stainless steel plates which were subsequently pressed against each other and combined together.

In order to evaluate performance of the photoreactive adhesive compositions obtained in Examples 10-16 and Comparative Examples 4-7, measurement of (3) gel fraction, (4) initial bond strength and (5) bond strength afer cure for those compositions was carried out. The results are listed in Tables 4 and 5. The following procedures were utilized to measure (4) initial bond strength and (5) bond strength after cure.

(Preparation of Test Samples)

Under a 23° C. atmosphere, each of the above-obtained photoreactive adhesive compositions was coated on a 3 cm×3 cm surface area of a polished stainless steel plate (3 cm×10 cm×0.2 cm) to a film thickness of 50 μm. The coated film was then exposed to a radiation at 50 mW/cm² using a high-pressure mercury lamp (JET LIGHT-2300", manufactured by ORC manufacturing Co., Ltd.) for 1 minute. Another polished but differently-sized stainless steel plate was placed to sandwich the coating film between the two stainless steel plates which were subsequently pressed against each other and combined together.

(4) Initial Bond Strength

Each test sample was left to stand at room temperature for 30 minutes and then its shear bond strength was measured at a cross-head speed of 5 mm/min to thereby determine initial bond strength.

(5) Bond Strength After Cure

Each test sample was aged at 23° C. for 7 days and then its shear bond strength was measured at a cross-head speed of 5 mm/min to thereby determine bond strength after cure.

TABLE 4

|  |  | Ex. |  |  |  |  | Comp. Ex. |  |
|---|---|---|---|---|---|---|---|---|
|  |  | 10 | 11 | 12 | 13 | 14 | 4 | 5 |
| Prepolymer (1) | (Parts by Weight) | 100 | 100 | 100 | 100 | 100 | 100 | 100 |
| Compound 1 |  | 5 | — | — | — | — | — | — |
| Compound 2 |  | — | 5 | — | — | — | — | — |
| Compound 3 |  | — | — | 10 | — | — | — | — |
| Compound 5 |  | — | — | — | 10 | — | — | — |
| Compound 6 |  | — | — | — | — | 10 | — | — |
| Compound A |  | — | — | — | — | — | 5 | — |
| Compound B |  | — | — | — | — | — | — | 5 |
| "DETX-S" |  | 0.5 | 0.5 | 0.5 | 0.5 | 0.5 | 0.5 | 0.5 |
| Gel Fraction (%) |  | 10 | 10 | 15 | 20 | 20 | 5 | 5 |
| Initial Bond Strength (N/cm²) |  | 29.4 | 29.4 | 29.4 | 44.1 | 49.0 | 9.8 | 9.8 |
| Bond Strength After Cure (N/cm²) |  | 294 | 294 | 392 | 392 | 441 | 294 | 294 |

TABLE 5

|  | Ex. |  | Comp. Ex. |  |
|---|---|---|---|---|
|  | 15 | 16 | 6 | 7 |
| Prepolymer (1) (Parts by Weight) | 100 | 100 | 100 | 100 |
| "AH600" | — | 5 | — | 5 |
| Compound 4 | 10 | 10 | — | — |
| Compound A | — | — | 10 | 10 |
| "DETX-S" | 0.5 | 0.5 | 0.5 | 0.5 |
| Gel Fraction (%) | 20 | 25 | 5 | 10 |
| Initial Bond Strength (N/cm²) | 29.4 | 49.0 | 9.8 | 24.5 |
| Bond Strength After Cure (N/cm²) | 294 | 294 | 294 | 294 |

As apparent from Tables 4 and 5, the photoreactive adhesive composition of Examples 10-14 all exhibit more suitable levels of crosslinking and improved gel fractions, compared to those of Comparative Examples 4-7. Such improved gel fractions indicate high initial strengths, leading to a marked improvement in applicability of the photoreactive adhesive compositions. The results clearly indicate that these performance differences are created by the existence of the carbamoyloxyimino-containing compound which generates amine upon exposure to a radiation. Also, the polyfunctionality of the carbamoyloxyimino-containing compound improves curing characteristics.

It is further demonstrated from comparison of Examples 15 and 16 to Comparative Examples 6 and 7 that the addition of the compound having a free-radically polymerizable group increases a gel fraction of the resulting composition, resulting in obtaining high initial bond strength.

The invention claimed is:

1. A photocurable composition characterized as containing:
    A: an amine-curable compound; and
    B: a photosensitive amine generator having a carbamoyloxyimino group; and
    a thioxanthone compound as a photosensitizer,
        said compound B having a carbamoyloxyimino group comprising a polymer or oligomer made via copolymerization of a compound having a free-radicaly polymerizable group with a monomer having a (meth) acryloyl group and a carbamoyloxyimino group.

2. The photocurable composition of claim 1, wherein said photosensitizer is incorporated in an amount of 1-100 parts by weight based on 100 parts by weight of said photosensitive amine generator.

* * * * *